United States Patent
Huber et al.

(10) Patent No.: US 10,052,627 B2
(45) Date of Patent: Aug. 21, 2018

(54) MEASURING ARRANGEMENT HAVING A SUPPORT ELEMENT AND A SENSOR

(71) Applicant: Endress + Hauser Flowtec AG, Reinach (CH)

(72) Inventors: Christof Huber, Bern (CH); Hagen Feth, Freiburg (DE); Frank Steinhoff, Staufen im Breisgau (DE); Holger Reinecke, Freiburg (DE)

(73) Assignee: ENDRESS + HAUSER FLOWTEC AG, Reinach (CH)

( * ) Notice: Subject to any disclaimer, the term of this patent is extended or adjusted under 35 U.S.C. 154(b) by 36 days.

(21) Appl. No.: 15/029,154

(22) PCT Filed: Sep. 10, 2014

(86) PCT No.: PCT/EP2014/069265
§ 371 (c)(1),
(2) Date: Apr. 13, 2016

(87) PCT Pub. No.: WO2015/055353
PCT Pub. Date: Apr. 23, 2015

(65) Prior Publication Data
US 2016/0256867 A1 Sep. 8, 2016

(30) Foreign Application Priority Data
Oct. 18, 2013 (DE) .................. 10 2013 017 317

(51) Int. Cl.
*G01D 11/30* (2006.01)
*B01L 3/00* (2006.01)
(Continued)

(52) U.S. Cl.
CPC ......... *B01L 3/502* (2013.01); *B01L 3/502715* (2013.01); *B01L 9/52* (2013.01);
(Continued)

(58) Field of Classification Search
CPC ...... B01L 3/502; B01L 3/502715; B01L 9/52; B01L 2300/0887; B01L 3/565;
(Continued)

(56) References Cited

U.S. PATENT DOCUMENTS 6,425,294 B1 * 7/2002 Shiono ................ G01L 19/0038
361/823
7,004,198 B1 2/2006 Okandan et al.
(Continued)

FOREIGN PATENT DOCUMENTS

CN 1499949 A 5/2004
CN 1942305 A 4/2007
(Continued)

OTHER PUBLICATIONS

English Translation of International Preliminary Report on Patentability, WIPO, Geneva, Apr. 28, 2016.
(Continued)

*Primary Examiner* — Robert R Raevis
(74) *Attorney, Agent, or Firm* — Bacon & Thomas, PLLC

(57) ABSTRACT

A measuring arrangement comprising: a support element having a longitudinal axis, wherein a sensor for ascertaining a process variable of a gaseous or liquid fluid is arranged on the support element; and the sensor, wherein the sensor has a fluid duct, which extends within the sensor. The support element has a fluid duct, and for mechanical connection of the fluid duct with the fluid duct of the sensor a bonding layer, which extends over a portion of a surface of the support element and over a portion of a surface of the sensor. The bonding layer comprises at least one fluorinated polymer. The support element has for connection of the fluid duct of the support element with the fluid duct of the sensor, in each case, at least one connection element, which protrude from the support element perpendicularly to the longitudinal
(Continued)

axis and which protrude inwardly into the fluid duct of the sensor. The connection elements are secured at least to a the sensor by means of a bonding layer, and wherein the bonding layer comprises a fluorinated polymer.

21 Claims, 4 Drawing Sheets

(51) Int. Cl.
*B01L 9/00* (2006.01)
*G01N 30/60* (2006.01)
(52) U.S. Cl.
CPC .............. *G01D 11/30* (2013.01); *B01L 3/565* (2013.01); *B01L 2200/026* (2013.01); *B01L 2200/0689* (2013.01); *B01L 2300/0627* (2013.01); *B01L 2300/0645* (2013.01); *B01L 2300/0832* (2013.01); *B01L 2300/0887* (2013.01); *B01L 2300/12* (2013.01); *G01N 2030/6013* (2013.01)
(58) Field of Classification Search
CPC ....... B01L 2200/026; B01L 2200/0689; B01L 2300/0645; B01L 2300/12; B01L 2300/0627; B01L 2300/0832; G01N 2030/6013; G01D 11/30
USPC .......... 73/865.8, 861–861.94, 273, 700–756, 73/863–866.5; 374/147, 148, 208
See application file for complete search history.

(56) References Cited

U.S. PATENT DOCUMENTS

| | | | |
|---|---|---|---|
| 7,005,857 B2 | 2/2006 | Stiene | |
| 8,444,835 B2 | 5/2013 | Elibol et al. | |
| 8,747,973 B2 | 6/2014 | Shimono et al. | |
| 2002/0155033 A1 | 10/2002 | Strand et al. | |
| 2005/0257885 A1 | 11/2005 | Hobbs | |
| 2007/0166497 A1 | 7/2007 | Shimono et al. | |
| 2007/0275193 A1 | 11/2007 | DeSimone | |
| 2008/0200343 A1 | 8/2008 | Clements et al. | |
| 2009/0298059 A1 | 12/2009 | Gumbrecht et al. | |
| 2010/0077862 A1* | 4/2010 | Benzel | G01L 19/0627 73/715 |
| 2012/0061239 A1 | 3/2012 | Elibol et al. | |
| 2013/0041236 A1 | 2/2013 | Pugia et al. | |
| 2013/0228950 A1 | 9/2013 | DeSimone et al. | |
| 2016/0061639 A1 | 3/2016 | Wiest et al. | |

FOREIGN PATENT DOCUMENTS

| | | |
|---|---|---|
| CN | 101189271 A | 5/2008 |
| CN | 103097881 A | 5/2013 |
| DE | 102011119472 A1 | 12/2012 |
| WO | 2014095115 A1 | 6/2014 |

OTHER PUBLICATIONS

International Search Report EPO, The Netherlands, Dec. 2, 2014.
German Search Report, German PTO, Munich, Dec. 3, 2013.
"A low temperature biochemically compatible bonding technique using fluoropolymers for biochemical microfluidic systems," Arum Han et al., Micro Electro Mechanical Systems MEMS 2000, pp. 414-418.
"Overview of the Development of the Fluoropolymer Industry," Hongxiang Teng, Appl. Sci. 2012, 2, www.mdpi.com/journal/appl. sci, pp. 496-512.

* cited by examiner

MEASURING ARRANGEMENT HAVING A SUPPORT ELEMENT AND A SENSOR

TECHNICAL FIELD

The present invention relates to a measuring arrangement comprising a support element and a sensor.

BACKGROUND DISCUSSION

A measuring arrangement of the field of the invention with a support element and a micromechanical sensor is disclosed in German Patent DE 10 2011 119 472 B3. This measuring arrangement includes especially in FIG. 1 a connection between the support element and the micromechanical sensor, wherein the connection is created by soldering. DE 10 2011 119 472 B3 additionally discloses that the soldered connection, referenced as chip holder, is also provided with supply and drain lines. Soldered connections have, however, the disadvantage that they are not sufficiently resistant to some fluids. This relates especially to chlorine containing fluids, which can attack the metal solder connection by metal complexing.

SUMMARY OF THE INVENTION

It is, consequently, an object of the present invention, based on DE 10 2011 119 472 B3, to provide an alternative connection between a support element and a micromechanical sensor.

The present invention achieves this object by a measuring arrangement which includes in a first variant:
  a) a support element having a longitudinal axis A, wherein a sensor for ascertaining a process variable of a gaseous or liquid fluid is arranged on the support element, and
  b) the sensor,
  wherein the sensor has a fluid duct, which extends within the sensor from a fluid inlet to a fluid outlet, and
  wherein the support element has at least one fluid duct,
  wherein the support element has for mechanical connection of the fluid duct of the support element with the fluid duct of the sensor a bonding layer, which extends over a portion of a surface of the support element and over a portion of a surface of the sensor, wherein the bonding layer comprises at least one fluorinated polymer.

The fluorinated polymer enables an alternative bonding of the sensor to the support element. It is distinguished by, among other things, a high chemical resistance to a large number of fluids. The fluorinated polymer is especially a thermoplastic or thermoelastic polymer. The bonding layer preferably forms, in such case, a fluid conducting connection between support element and sensor, so that fluid can be transferred from the fluid duct of the support element to the fluid duct of the sensor.

A measuring arrangement of the invention includes in a second variant
  a) a support element having a longitudinal axis A, wherein a sensor for ascertaining a process variable of a gaseous or liquid fluid is arranged on the support element, and
  b) the sensor
  wherein the sensor has a fluid duct, which extends within the sensor from a fluid inlet to a fluid outlet, and wherein the support element has a fluid duct, and wherein the support element has for connection of the fluid duct of the support element with the fluid duct of the sensor, in each case, at least one connection element, which protrude from the support element perpendicularly to the longitudinal axis A and which protrude inwardly into the fluid duct of the sensor and wherein the connection elements are secured at least to the sensor by means of a bonding layer, and wherein the bonding layer comprises a fluorinated polymer.

The measuring arrangement of the invention providing a fluid conducting connection of the support element to the sensor has a more defined dead volume compared with a conventional connection.

In such case, the sensor is mechanically connected with respective connection elements by means of a bonding layer of a thermoplastic polymer.

It is advantageous to have the connection elements form one-piece with the support element. An especially preferred connection element of one-piece with the support element can be manufactured by means of a primary forming method, preferably by means of cold deformation, such as e.g. a compressive rolling method, or a machining method, such as known for vehicle construction (e.g. German Patent DE 10 2006 011 021 A1).

Alternatively, a connection element can advantageously be embodied as a tubular component, which is arranged in the fluid duct of the support element. The connection element can have, in this case, for mechanical bonding of the connection element to the support element likewise a bonding layer of the mentioned polymer material at an exit opening of the fluid duct. In this way, an improved pressure resistance of the bonding of the connection element to the support element is achieved. In total, thus, the transition between sensor, connection element and support element preferably includes a unified bonding layer.

In the case that the connection element and the support element are embodied integrally as one-piece, then a bonding layer is only needed between the sensor and the connection element.

The thermoplastic polymer is preferably a copolymer with at least one polyfluorinated component. The copolymer is composed especially of chlorotrifluoroethylene and ethylene and especially preferably the copolymer is a 1:1 copolymer of chlorotrifluoroethylene and ethylene. In such case, the copolymer can be the Halar ECTFE product of Solvay Solexis.

Besides the copolymer, the bonding layer can contain yet other substances to warrant the term, plastic, substances such as antioxidants and UV stabilizers, which further increase the long term durability of the bonding layer against environmental influences. Additionally, conductive materials can, in given cases, be added to enable electrical continuity between sensor and support element.

Additionally or alternatively, also heat conductive materials, which increase thermal conductivity, can be added to the plastic, in order to increase heat transfer between the support element and the sensor.

Additionally or alternatively, also magnetic substances can be added to the plastic, in order to provide magnetic continuity between sensor and support element. Corresponding magnetic substances can include e.g. magnetite particles.

The bonding layer in a preferred embodiment, however, contains at least 80 wt-%, preferably more than 90 wt-%, of the copolymer compound, wherein weight fractions of possible fillers are not taken into consideration in the case of this data.

The bonding layer can contain besides the polymer supplementally also the mentioned fill substances, e.g. as particulate fill substances, i.e. substances such as calcium carbonate or soot. These can be added to the extent that the polymer can hold them.

The support element can additionally have a connection element for transfer of the fluid from the support element into the sensor, wherein the connection element has the bonding layer at least in certain regions on its perimeter. This means that the bonding layer, in this case, performs the mechanical bonding of the connection element to the sensor. At the same time, it can seal the transition between connection element and sensor. The connection element can be of a corrosion resistant metal, preferably steel, especially stainless steel. Especially preferable in such case is stainless steel of type PH 17-4. This material is, on the one hand, corrosion resistant and, on the other hand, has a thermal coefficient of expansion matched to the sensor material.

Ideally, the thermal coefficient of expansion of the material of the support element amounts advantageously to less than 7-times, preferably less than the 5-times, the thermal coefficient of expansion of the material of the sensor. The same holds for the optional connection element.

Advantageously arranged between the sensor and the support element are other material bonded connections for additional stabilizing. These also are embodied by means of fluorinated polymers. Alternatively, also a solder connection can be applied at a non-fluid contacting position.

To the extent that instead of a direct bonding between sensor and support element by means of the bonding layer a connection element is utilized, such can advantageously be formed from the support element by means of a primary forming method.

Alternatively, the connection element also can be embodied as a tubular component, which is arranged in the fluid duct of the support element. This is especially advantageous, when the separation between sensor and support element should be embodied variably depending on dimensioning of the measuring arrangement.

It is advantageous to have the fluid duct of the support element be lined with the fluorinated polymer. Thus, not only the region of the transition to the sensor, but also the material of the support element as a whole is protected by the polymer layer from direct contact with the medium.

The bonding layer can in the case of the optional application of a connection element be provided either only between sensor and connection element or between sensor, connection element and support element and can supplementally be reinforced as regards its mechanical strength by a solder connection.

Especially advantageous is when the aforementioned material bonded connections are distributed as uniformly as possible in the region between the sensor and the support element. Therefore, it is advantageous, when the surface of the sensor facing the support element is divisible into at least three equally dimensioned sensor sections, wherein at least two of the three sensor sections have, in each case, at least one of the material bonded connections.

BRIEF DESCRIPTION OF THE DRAWINGS

The invention will now be explained in greater detail based on the appended drawing, the figures of which show as follows.

DETAILED DISCUSSION IN CONJUNCTION WITH THE DRAWINGS

The measuring arrangements illustrated in FIGS. 1-6 are preferably applied in measuring devices of process- and automation technology.

The present invention relates to bonding of a sensor to a support element. The sensors in the following examples of embodiments are micromechanical sensors. The invention is, however, not limited to micromechanical sensors.

The base area of a preferred sensor can preferably correspond to the area of a wafer. The base area is, in such case, the area, over which the sensor can be connected with the support element.

Especially preferably, at least one edge length of the sensor is less than or equal to 10 cm. Quite especially preferably, all edge lengths of the sensor are less than or equal to 10 cm.

Figure 1:
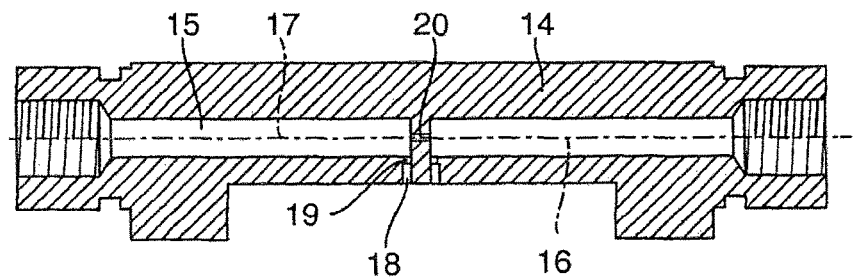
FIG. 1 is a sectional view of a support element of a first measuring arrangement.

FIG. 1 shows an example of an embodiment of a sensor, for example, in the form of a sensor for a Coriolis mass flow measuring device in micromechanical construction (MEMS—micro electro mechanical system).

FIG. 1 shows a corresponding support element 14 having a longitudinal axis A, wherein a micromechanical sensor can be arranged on the support element 14 for ascertaining a process variable of a gaseous or liquid fluid.

The process variable can preferably be the density, the viscosity, the composition, the volume flow, the mass flow, the temperature and/or the flow velocity of a fluid.

Support element 14 includes a fluid duct, which is divided into a fluid supply duct 15 and a fluid drain duct 16. The fluid supply duct 15 is for delivery of the fluid to the sensor. Fluid supply duct 15 includes in the example of an embodiment illustrated in FIG. 1 a first duct segment 17, which extends essentially parallel to the longitudinal axis A of the support element 14. This duct segment is connectable terminally with a process connection of a pipeline. The fluid supply duct includes additionally a second duct segment 18, into which the first duct segment 17 opens. This second duct segment 18 in the present example of an embodiment is arranged at an angle of 90° to the longitudinal axis in the support element 14. In such case, the diameter of the first duct segment 17 is larger, preferably at least twice as large, than the diameter of the second duct segment 18. The second duct segment 18 includes a diameter expansion 19 for accommodating a connection element. In this way, there occurs after the insertion of the connection element no nominal diameter jump within the second duct segment 18. The second duct segment 18 permits fluid to be conducted out from the support element in a direction radial to the axis.

Support element 14 includes additionally a fluid drain duct 16, which is of essentially equal construction to that of the fluid supply duct 15. Between the fluid drain duct and the fluid supply duct, optionally a duct connection segment 20 can be arranged, which is arranged in the support element 14 parallel to the longitudinal axis A and connects the fluid supply duct and the fluid drain duct with one another. Thus, the entire fluid stream does not have to be directed through the micromechanical sensor, but, instead, only a part of the fluid. The nominal diameter of the duct connection segment has, in such case, a smaller diameter than the first duct segment 17. Preferably, the nominal diameter of the duct connection segment is one half that of the first duct segment 17, or smaller.

Figure 2:
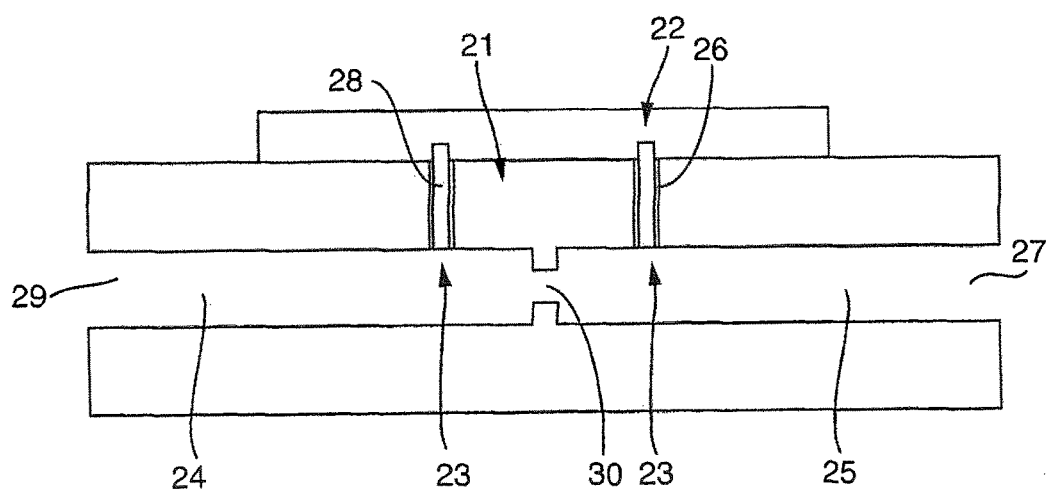
FIG. 2 is a schematic sectional view of the measuring arrangement.

FIG. 2 shows a schematic structure of a first measuring arrangement 31. A measuring arrangement of the invention includes at least one support element 21, a micromechanical sensor 22 and connection elements 23, which connect the support element 21 and the sensor 22 with one another, in such a manner that the connection elements 23 protrude into the micromechanical sensor 22, respectively into a fluid duct arranged therein.

Sensors, especially micromechanical sensors, such as can be applied in the present example, are known per se. The sensors installed in the present example can be formed as Coriolis flow measuring devices, as magneto-inductive flow measuring devices, as thermal flow measuring devices, as pressure measuring devices, as viscosity measuring devices, spectroscopic measuring devices, ultrasonic measuring devices, especially ultrasonic, flow measuring devices, density measuring devices and measure process variables such as viscosity, density, pressure, composition, temperature, viscosity and, in given cases, also flow. The terminology, sensors, includes in the context of present invention also chromatographic analyzers (LC- or GC analyzers).

Support element 21 includes a fluid supply duct 24 and a fluid drain duct 25. These have, in each case, a first duct segment 27, 29 parallel to the longitudinal axis A and a second duct segment 26 and 28, which extends radially from the longitudinal axis through the support element 21. Also, in the example of an embodiment set-forth in FIG. 2, a duct connection segment 30 is arranged between the first duct segments 27 and 29 of the fluid supply duct 24 and the fluid drain duct 25.

In contrast to FIG. 1, support element 21 includes no diameter widening 19. Rather, the connection elements 23 are inserted completely into the second duct segments 26 and 28.

The sensor is preferably manufactured of a glass or silicon material. Typically, the coefficient of thermal expansion in the case of these materials amounts to, for instance, $3*10^{-6}$ $K^{-1}$. Alternatively, also sensors of ceramic materials are suitable for these applications. The connection elements 23 are embodied either as individual components in the form of small tubes or integrally formed, such as is explained in greater detail with reference to FIG. 5. They are preferably composed of stainless steel—preferably type PH 17-4. Other materials, for example, plastics, provide alternative options. Especially in the case of hot or cold fluids, it is, however, advantageous to have the thermal coefficients of expansion of the materials of the sensor and the connection element differ from one another by no more than 5-times. Otherwise, unsealed locations can occur in the case of higher pressures or the sensor can even come loose. Stainless steel of type pH 17-4 fulfills these requirements relative to a silicon material and/or glass material (including borosilicate glass). To the extent that the connection elements are embodied integrally with the support element, the material of the support element should naturally correspond the material of the connection elements. To the extent that, however, the connection elements 23 are provided as individual components in the support element 21, then the material of the support element can preferably be selected from more cost effective materials, for example, stainless steel of type 316 L. Alternatively, also other materials, especially titanium zirconium, tantalum, silicon or conducting ceramic material, can be applied for the support element and/or the connection element.

In a special embodiment, an internal coating of the connection element or the connection element as a whole is composed of a polymer selected from the following materials: PE, PEEK, PFA, PTFE, PBT PEK or, especially preferably of a copolymer, for instance a 1:1 copolymer of chlorotrifluoroethylene and ethylene, especially the Halar ECTFE product of Solvay Solexis. This has special advantages as regards process for its application. It has, among other things, compared with a soldered connection, better surface wetting and adhesion on the surface of the sensor and is chemically resistant to chlorine containing compounds. For example, in the case of measuring chlorine containing compounds, it is additionally advantageous also to line the fluid supply duct and the fluid drain duct with the aforementioned copolymer, i.e. a 1:1 copolymer of chlorotrifluoroethylene and ethylene, especially the Halar ECTFE product of Solvay Solexis.

Additionally advantageously arranged between the support element and the connection element and the support element and the sensor can be a supplemental sealing in the form of a membrane structure or a sealing lip, so that the bonding layer is not excessively mechanically or chemically loaded.

Before application of the bonding layer, it is helpful to treat the surfaces to be connected, in order to enable a better clinging. This can occur chemically by etching or by corona discharge or lasers or by abrasive methods such as e.g. sand blasting. The treated surfaces can then be wetted better by the thermoplastic bond material.

The connection elements 23 especially enable a fluid flow connection between micromechanical sensor 22 and the support element 21. However, it is helpful, especially in the case of higher pressures, to provide additional mechanical connection of the micromechanical sensor 22.

The schematic drawing of FIG. 2 does not show detail of the mechanical bonding of the micromechanical sensor 22 to the support element 21.

Figure 3:
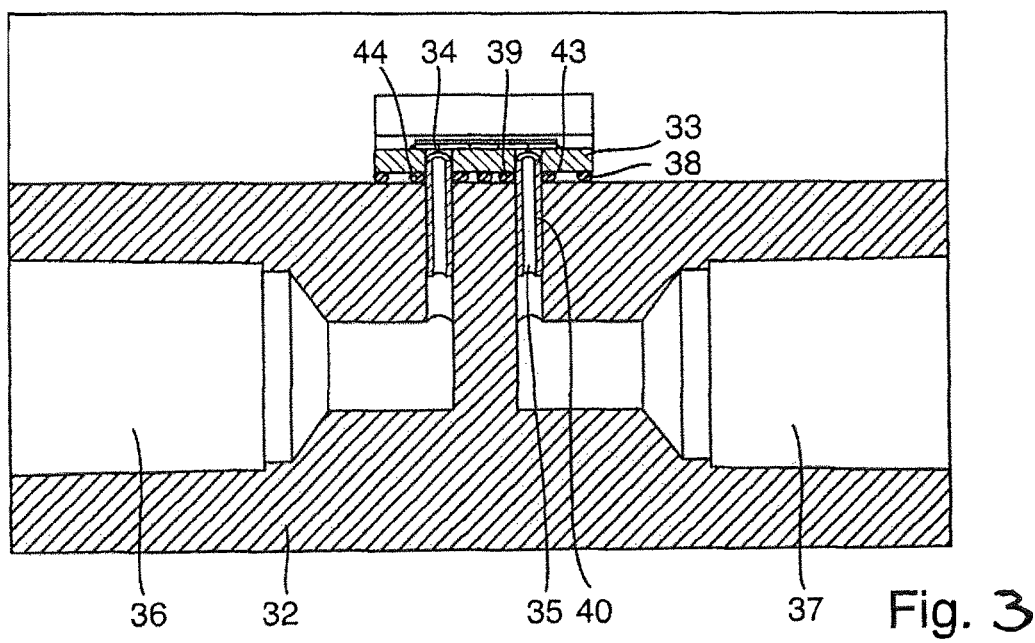
FIG. 3 is a schematic sectional view of the measuring arrangement in perspective.
Figure 4:
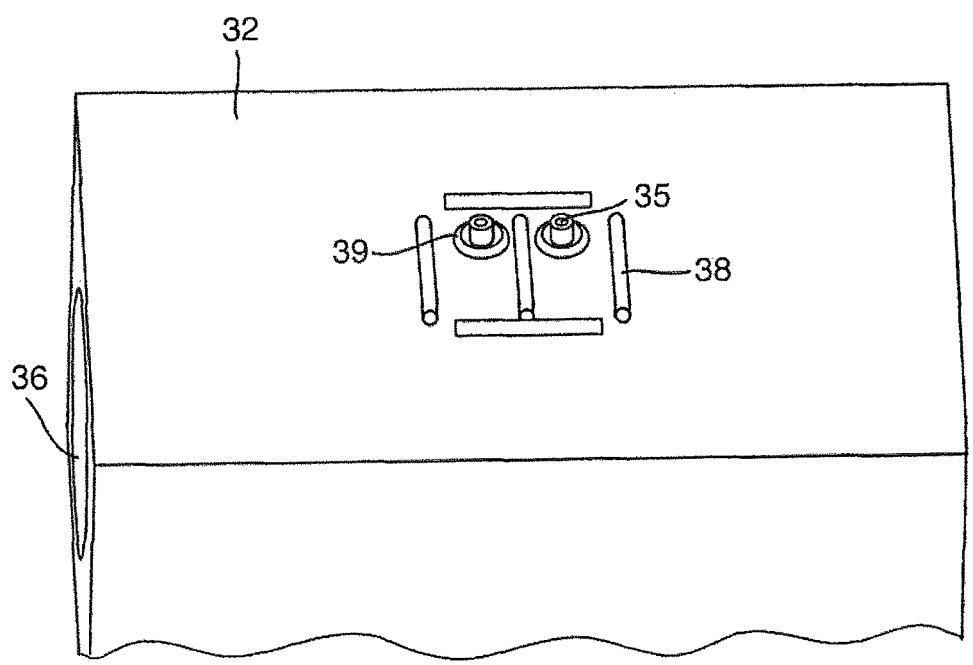
FIG. 4 is a schematic representation of the support element of the measuring arrangement with a bonding layer of a fluorinated polymer.
Figure 5:
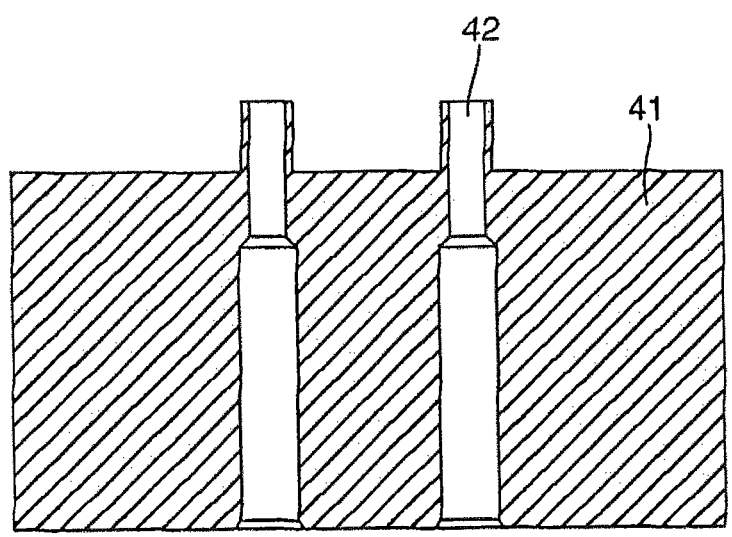
FIG. 5 is a schematic representation of a second measuring arrangement.

An embodiment of the mechanical bonding will now be explained in greater detail with reference to FIGS. 3 and 4. FIGS. 3 and 4 show analogously to FIG. 2 a support element 32 with a fluid supply duct 36 and a fluid drain duct 37. Arranged in these channels 36 and 37 are, in each case, connection elements 35. FIG. 3 shows additionally a micromechanical sensor 33 with a therein arranged fluid duct 34, which extends from a fluid inlet 44 to a fluid outlet 43 and into which the connection elements 35 protrude.

The mechanical bonding of the micromechanical sensor occurs in the example of an embodiment shown in FIGS. 3 and 4 by means of a bonding layer. This bonding layer of fluorinated plastic in FIGS. 3 and 5 can be deposited with targeting on the surface of the support element and/or of the sensor in a material saving manner by means of a deposition mask.

FIGS. 1-5 show connection elements between the sensor and the support element. However, the subject matter of the present invention includes also an embodiment, in which the sensor and the support element are connected with one another directly by means of the aforementioned copolymer plastic. In such case, the connection elements can be omitted.

Figure 6:
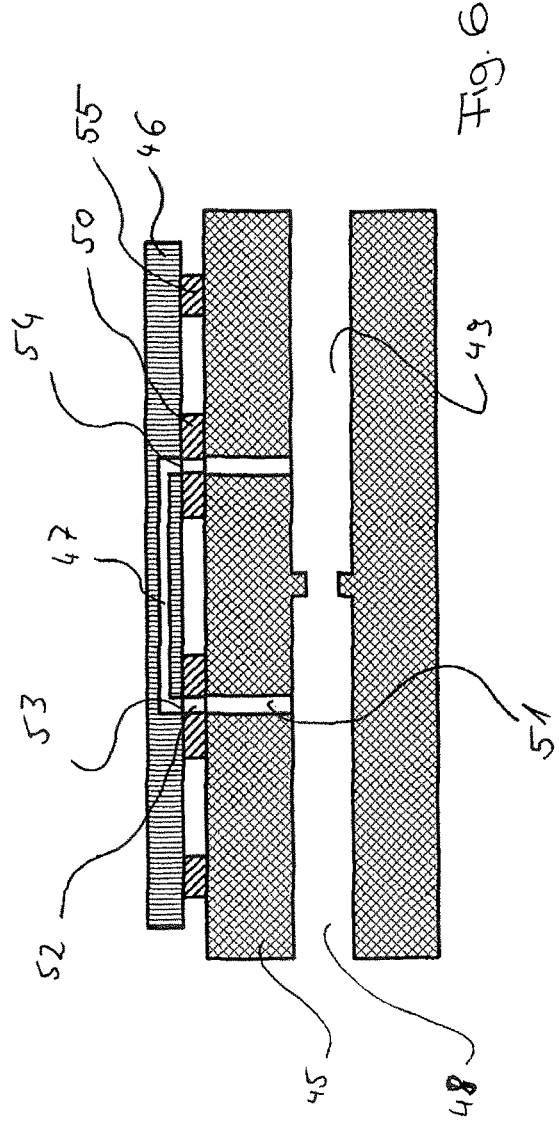
FIG. 6 is a schematic arrangement of a third measuring arrangement.

FIG. 6 shows a third variant of a measuring arrangement comprising a support element 45 and a sensor 46, which has a fluid duct 47 with a fluid inlet 53 and a fluid outlet 54.

The fluid duct of the support element is divided as in the previous examples into a fluid supply duct 48 and a fluid drain duct 49. Analogously to the previous examples of embodiments, the fluid supply and drain ducts communicate with two duct segments, a first duct segment and a second duct segment. In this instance, however, the second duct segment 51 has no connection element, but, instead, a mechanical bonding layer 55. The bonding layer 55 between the support element 45 and the sensor 46 is embodied as a fluorinated polymer 55 comprising a copolymer. This includes a fluid conducting connection 52, which connects the fluid duct 47 of the sensor 46 and the fluid duct of the support element 45.

Arranged between the sensor 46 and the support element 45 are other connections 55, which enable an improved mechanical bonding of the sensor to the support element The fluid conducting connections provided either by the connection element or by the mechanical bonding layer, as shown in FIGS. 1-6, have preferably a cross sectional area of less than 1000 mm$^2$, especially preferably 100 mm$^2$ and especially 20 mm$^2$.

A preferred coating thickness of the bonding layer amounts to less than 1 mm, preferably less than 200 µm and especially preferably less than 100 µm. An especially preferred coating thickness of the mechanical bonding layer lies in the range between 100 nm and 100 µm.

In addition to the mechanical bonding layer in the examples of embodiments of FIGS. 1-6, also solder rings and solder wires, blanked metal foils, especially gold and/or tin foils, and/or an electrochemically deposited layer or layers, especially a gold layer, can care for a secure bonding and supplement the polymer layer. The polymer, respectively copolymer, can additionally be applied on the respective substrate by means of a template. Alternatively, however, less preferably compared with gold material, also tin material can be utilized for forming connections.

Suited as solder material is especially preferably a noble metal, e.g. silver or gold or noble metal containing alloys. Thus, for example, also eutectic mixtures of silver and tin are applicable. The shrinkage of these materials amounts, in such case, to preferably less than 1 vol-%.

Substances, which improve the electrical, thermal and/or magnetic conductivity of the bonding layer, can be added to the fluorinated polymer. Alternatively or supplementally, also substances, which enable a better thermal expansion accommodation of the materials of the support element and the sensor, can be added to the polymer.

Substances for improving the electrical conductivity are preferably solderable and at the same time conductive, such as the already earlier mentioned substances.

Substances in, which can improve the thermal conductivity, are, for example, silicon carbide and/or aluminum nitride.

Substances, which can enable a better thermal expansion accommodation, are preferably corundum and/or aluminum oxide.

Substances, which can improve the magnetic conductivity, or permeability, are, for example, magnetite or magnetizeable metals or metal alloys.

In such case, it is advantageous to have the bonding layer of fluorinated plastic be less than ⅕ mm thick, preferably less than 1/10 mm.

In a special embodiment, the mechanical bonding layer can be transparent, in such a manner that optical components, e.g. optical sensors, can be connected to the mechanical bonding layer, wherein the bonding layer is embodied as a light conductor. For this, the bonding layer can comprise additional opticallty functional materials.

The aforementioned mechanical bonding layers 38 and 39 are shown in FIGS. 3 and 4. In such case, the mechanical bonding layer 38 is arranged in the region of the connection elements for transfer of the fluid from the support element to the sensor. Optionally, the bonding layer 39 is also arranged in the form of connecting points in non-medium-contacting regions between the sensor and the support element. As one can see, consequently, these bonding layers need not completely cover the surface of the carrier material or the sensor, but, instead, can also be provided only at selected connecting points between the two components.

The mechanical bonding layer can be applied on the support element and/or on the sensor in many different ways. These can include especially electrostatic coating, powder coating, powder injecting or, in liquid form, so-called dip coating.

In the following, an especially preferred example of an embodiment of a method for manufacture of a mechanical connection between the support element, the one or more connection elements and/or the sensor by means of the fluorinated polymer will now be described in greater detail.

FIG. 6 shows a further example of an embodiment of a measuring arrangement of the invention, wherein in the case of this arrangement no connection elements are used.

In such case, a support element 45 is connected with a sensor 46 by means of a mechanical bonding layer 50. The sensor 46 includes a fluid duct 47 with a fluid inlet 53 and a fluid outlet 54.

Support element 45 includes a fluid duct, which is divided into a fluid supply duct 48 and a fluid drain duct 49 and a first duct segment and a second duct segment 51.

The mechanical bonding layer 50 between the support element 45 and the sensor 46 is composed preferably of a fluorinated copolymer and connects the fluid duct 47 of the sensor 45 with the fluid duct of the support element 45. For this, the bonding layer 50 includes a fluid conducting connection 52, which is embodied as a hole in the bonding layer. Through this hole, a fluid can be transferred loss-free from the support element to the sensor and back.

The fluorinated plastic can also form a mechanical connection 55 between the sensor and the support element at additional locations.

The steps of the manufacturing process include that, by depositing a The steps of the manufacturing process include that, by depositing a polymer layer of the fluorinated polymer in the region of the exit openings of the fluid duct of the support element, a connecting layer to the connection elements (tubelets) between the support element and the sensor can be created.

Alternatively, by depositing the mentioned polymer layer in the absence of the connection elements, a connection, especially a fluid conducting connection, can be created between the support element and the sensor.

After the depositing of the polymer layer, a heating of the polymer layer occurs. Then, the sensor or the mentioned connection elements can be arranged at and/or on the support element, so that upon cooling a mechanical connection results between the support element and the sensor and/or between the support element and the connection elements and/or between the connection elements and the sensor. In the latter case, the connection elements are earlier secured to the support element.

In an especially preferred method for manufacturing a mechanical connection between a support element, a sensor and/or a connection element, in a portion of the substrate, thus the support element, the connection element or the sensor, the fluorinated polymer is applied electrophoretically as a polymer layer. Electrophoretic deposition has proven to be especially suitable.

The polymer material applied on the substrate is heated, in order to bring about a change in the viscosity of the polymer material. The component is arranged on the heated polymer material, so that a surface of the component is wetted by the polymer material with the changed viscosity. Subsequent cooling of the polymer material effects the mechanical connection between the substrate and the component.

Advantageous with this form of embodiment is that the substrate, preferably the support element, can be transported as a preliminary product with the applied polymer material, for instance, from a location of manufacture of the preliminary product to a location of further processing. Furthermore, the manufacture of the mechanical connection can occur by a heating and a cooling, so that complex adhesive processes, which can require monitoring of humidity and/or cure times, or open the possibility of damage to the substrate, can be omitted.

A possible course of an embodiment of a manufacturing method will now be described in detail based on the example of manufacture of a fluid conducting connection between support element and sensor.

In a first step, a fluorinated polymer, for example, the Halar ECTFE product, is deposited electrophoretically on the carrier material in the region of an output opening of the fluid duct of the support element, i.e., electrophoretic deposition (EPD) is applied for deposition of the polymer material on the substrate. The application can occur in the form of one or more plies. The thicknesses of the one or more plies can be equal or differ from one another, so that a resulting total thickness can be variably adjustable.

Different materials can vary via different applied plies of polymer material and/or within an applied ply of the polymer material. Thus, for example, a ply arranged on the surface of the support element can have an especially good adhesive characteristic for the material of the support element and a ply arranged thereon can have a desired elastic property. Alternatively, the polymer material in a ply can have additives, which give this ply different properties in certain regions. These can be e.g. electrically conductive additives.

For example, in this way, a voltage conducting connection and a ground connection can be embodied by the polymer-based plastic material, wherein the two connections are insulated from one another by the pure in polymer material.

Application of the polymer material by EPD can enable reduction of defects in the polymer material and/or the substrate surface. Due to the large mass transfer, which EPD allows, for example, defects in the surface of the support element, such as e.g. scratches, can be healed, respectively cancelled, so that slight irregularities of the substrate surface are covered by a polymer layer with a more planar surface. In other words, EPD can enable a compensation of topography changes on the substrate surface.

Furthermore, EPD permits both thin as well as also uniform layer thicknesses coupled with an, in given cases, reduced scope of defects compared with other coating methods. Layer thicknesses of the polyfluorinated plastic are implementable, for example, in a range from 0.01 to 300 µm. A combination of plies permits also greater material thicknesses, for example, in the millimeter range.

EPD enables thin layer thicknesses, among other things, due to a good controllability of the electrostatic coating process, especially the electrostatic fields, which are utilized for depositing the polymer material. The electrophoretically deposited material need, in such case, not absolutely be formed by the deposition of colloidal particles.

In order to apply the polymer material on the substrate, an electrostatic field can be placed between the substrate, respectively an anode arranged thereon or neighboring thereto, and a corresponding cathode. Thus, for example, an electrically conductive component of the substrate can form the anode. With an electrical voltage applied between the anode and the cathode in a bath, which has the polymer distributed in the form of particles in the bath, a coating of the substrate with the polymer material can occur in the region of the anode. The particles can be colloidally formed, so that a smooth surface of the deposited polymer can be formed, respectively the surface roughness or the number of defects in the polymer material is reduced.

In an additional step, the fluorinated plastic is heated, at least sufficiently to bring about a change of the viscosity of the polymer material. Upon reaching the respective melting temperature of the polymer, such can, for example, transfer into a liquid or viscous state. In other words, the polymer material is melted. In an especially preferred embodiment, the fluorinated plastic is melted by heating at temperatures, which preferably lie less than 30K, especially preferably less than 20K, above the melting temperature of the fluorinated plastic material. In this way, shape is essentially retained and the surface begins to liquefy, whereby a wetting of the plastic material on the sensor surface is achieved.

In an additional step, the sensor is arranged on the heated, fluorine-containing plastic material. For example, the sensor can be pressed onto the support element or the support element can be pressed onto the sensor. Alternatively, an option is to use a tensile force to arrange the component on the heated polymer material.

Upon a cooling of the polymer material, such as, for instance, by active cooling in a cooling or climate chamber or by leaving the polymer material at room temperature, the polymer material can show a renewed change of viscosity, when the temperature of the polymer material sinks below the melting temperature. The cooling of the polymer material, respectively the thereby induced change of the viscosity, leads to the mechanical connection between the support element and the sensor. Such a mechanical connection can leave the substrate undamaged and enable a fast and/or cost effective forming of the connection.

The polymer material can be so selected that the viscosity of the polymer material, compared with the viscosity before the heating, has after cooling back to a starting temperature a changed or an approximately equal viscosity. Thus, for example, thermoactive components in the polymer material can react during the heating or the connecting with the component and after cooling of the polymer material form a partially crystalline structure. Alternatively, additional cross-linking reactions, especially cross-linking reactions caused by supply of thermal energy, can be activated.

Alternatively, the polymer material can also approximately return to its starting state. In principle, a renewed warming of the polymer material can lead to a new change of the viscosity, in order to release the component from the substrate or to shift the component. A releasing of the connection can enable, for example, replacement of an aged or defective sensor.

After heating the fluorinated plastic to its melting temperature, the copolymer can be further heated, until a reaction temperature of components of the polymer material is achieved, so that these components form a crystalline structure. A crystalline structure can lead to a mechanical connection with a greater strength and/or stiffness compared with other components of the polymer material.

For forming the fluid conducting connection, an as exact as possible shape or geometry of the polymer layer on the substrate can be desirable and preferable. If, for example, a medium, such as, for instance, water, another liquid, or wind, flows past the mechanical connection in a later application, protrusions or material overhangs can form points of engagement for erosion. A defined geometric structuring of the polymer layer can reduce or avoid these points of engagement and, in given cases, enable material savings. A desired geometry of the polymer layer can be achieved, for example, by making an anode form applied for the EPD correspond approximately to the surface form of the component, thus of the sensor, which later is to be arranged on the support element, respectively on the polymer layer, so that the polymer can already be deposited with a desired accuracy on the substrate. Alternatively, an option is likewise that, for example, a mask is arranged on the substrate, before or while the EPD is performed, so that the mask prevents deposition of the polymer material on undesired locations on the substrate and enables a structured arrangement of the polymer material. Alternatively, an option is that the polymer material is deposited, respectively arranged, with an arbitrary or permitted inaccuracy on the substrate and in a following process step further worked, for example, by etching or milling, so that a desired geometry of the polymer layer on the support element is obtained. In other words, a part of the polymer layer is removed and consequently the polymer layer is structured, so that a structured region of the substrate surface is covered by the polymer material.

The invention claimed is:

1. A measuring arrangement comprising:
a support element having a longitudinal axis;
a sensor for ascertaining a process variable of a gaseous or liquid fluid arranged on said support element; and
said sensor has a fluid duct, which extends within said sensor, wherein:
said support element has a fluid duct;
said support element has for mechanical connection of said fluid duct of said support element with said fluid duct of said sensor a bonding layer, which extends over a portion of a surface of said support element and over a portion of a surface of said sensor; and
said bonding layer comprises at least one fluorinated polymer.

2. The measuring arrangement as claimed in claim 1, wherein:
said fluorinated polymer is a copolymer having at least one polyfluorinated component.

3. The measuring arrangement as claimed in claim 2, wherein:
said copolymer is composed of chlorotrifluoroethylene and ethylene.

4. The measuring arrangement as claimed in claim 3, wherein:
said copolymer compound is a 1:1 copolymer of chlorotrifluoroethylene and ethylene.

5. The measuring arrangement as claimed in claim 1, wherein:
said bonding layer contains at least 80 wt-%, of the copolymer.

6. The measuring arrangement as claimed in claim 1, wherein:

said support element has a connection element for transfer of the fluid from said support element into said sensor; and
said connection element has said bonding layer at least in certain regions on its perimeter.

7. The measuring arrangement as claimed in claim 6, wherein:
said support element and/or said connection element are/is composed of metal.

8. The measuring arrangement as claimed in claim 1, wherein:
the thermal coefficient of expansion of the material of said support element amounts to less than 7-times the thermal coefficient of expansion of the material of said sensor.

9. The measuring arrangement as claimed in claim 1, wherein:
between said sensor and said support element at least one other material bonded connection is arranged, which is embodied by means of the fluorinated polymer.

10. The measuring arrangement as claimed in claim 1, wherein:
said fluid duct of said support element or of said sensor is lined at least in certain regions with the thermoplastic polymer.

11. The measuring arrangement as claimed in claim 1, wherein:
said bonding layer is constructed of at least two plies.

12. The measuring arrangement as claimed in claim 11, wherein:
said at least two plies have different properties.

13. The measuring arrangement as claimed in claim 1, wherein a mechanical bonding layer has a fluid conducting connection between said fluid duct of said sensor and said fluid duct of said support element.

14. The measuring arrangement as claimed in claim 1, wherein: the thermal coefficient of expansion of the material of said support element amounts to less than 5-times the thermal coefficient of expansion of the material of said sensor.

15. A measuring arrangement comprising:
a support element having a longitudinal axis;
a sensor for ascertaining a process variable of a gaseous or liquid fluid arranged on said support element; and
said sensor has a fluid duct, which extends within said sensor, wherein:
said support element has a fluid duct,
said support element has for connection of the fluid duct of said support element with the fluid duct of said sensor, at least one connection element, which protrude from said support element perpendicularly to the longitudinal axis and which protrude inwardly into the fluid duct of said sensor; and
said connection element is secured at least to said sensor by means of a bonding layer; and
said bonding layer comprises a fluorinated polymer.

16. The measuring arrangement as claimed in claim 15, wherein:
said at least one connection element is formed from said support element by means of a forming method.

17. The measuring arrangement as claimed in claim 15, wherein:
said at least one connection element is embodied as a tubular component, which is arranged in said fluid duct of said support element.

18. The measuring arrangement as claimed in claim 15, wherein:

said connection element is lined with the copolymer compound.

19. The measuring arrangement as claimed in claim 15, wherein:

said fluorinated polymer is a copolymer having at least one polyfluorinated component.

20. The measuring arrangement as claimed in claim 19, wherein:

said copolymer is composed of chlorotrifluoroethylene and ethylene.

21. The measuring arrangement as claimed in claim 20, wherein:

said copolymer compound is a 1:1 copolymer of chlorotrifluoroethylene and ethylene.

* * * * *